United States Patent [19]

Scholz

[11] Patent Number: 5,141,747
[45] Date of Patent: Aug. 25, 1992

[54] DENATURED COLLAGEN MEMBRANE

[75] Inventor: Matthew T. Scholz, St. Paul, Minn.

[73] Assignee: Minnesota Mining and Manufacturing Company, St. Paul, Minn.

[21] Appl. No.: 355,758

[22] Filed: May 23, 1989

[51] Int. Cl.$^5$ .................. A61F 2/18; A61K 37/12
[52] U.S. Cl. .................. 424/424; 514/2; 514/21; 514/801; 530/356; 530/402; 623/10; 623/66
[58] Field of Search .......... 530/356, 402; 514/2, 514/21; 623/10, 11, 15, 16, 66; 204/157.68; 424/424

[56] References Cited

U.S. PATENT DOCUMENTS

| | | | |
|---|---|---|---|
| 476,853 | 6/1892 | Wilson | 181/134 |
| 2,400,995 | 5/1946 | Humphner | 428/132 |
| 2,738,025 | 3/1956 | Annas | 181/134 |
| 3,073,714 | 1/1963 | Shu-Tung Tu et al. | 181/134 |
| 3,509,007 | 4/1970 | Kalwaites | 428/132 |
| 3,906,578 | 9/1975 | Huber | 15/104 R |
| 3,989,867 | 11/1976 | Sisson | 428/132 |
| 4,233,360 | 11/1980 | Luck et al. | 128/156 |
| 4,409,332 | 10/1983 | Jefferies et al. | 435/188 |
| 4,695,281 | 9/1987 | Miyata et al. | 623/11 |
| 4,713,446 | 12/1987 | DeVore et al. | 530/356 |

Primary Examiner—Thurman K. Page
Assistant Examiner—G. S. Kishore
Attorney, Agent, or Firm—Wegner, Cantor, Mueller & Player

[57] ABSTRACT

Disclosed is an artificial membrane comprising a product made by cross-linking molecules of interpenetrating denatured collagen coupled at their lysine epsilon amino groups with a coupler through carbonyl groups, sulfonyl groups, or combination thereof on the coupler wherein non-coupled lysine epsilon amino groups are bonded to a modifier wherein the modifier is a carbonyl sulfonyl, carbamoyl, or β-malic acid group.

38 Claims, No Drawings

DENATURED COLLAGEN MEMBRANE

The present invention relates to modified collagen In particular, it relates to modified collagen that can be formed into a sheet or film as a membrane for medical use.

Cohesive films of high tensile strength have been manufactured using collagen molecules. However, this involves cross-linking the collagen molecules with aldehydes, which can subsequently hydrolyze and leech out of the film. Because such residues are cytotoxic, these films make poor prosthetic articles.

Collagen molecules coupled and modified at their lysine epsilon amino groups exhibit physiological compatibility. Solutions and suspensions of these collagen molecules are useful in a variety of medical applications, e.g., in soft tissue augmentation and in ocular fluid replacement in ophthalmic surgery. However, due to a lack of mechanical strength, these solutions and suspensions are limited to applications that do not require cohesive stability.

Accordingly, the present invention is an artificial membrane comprising a product made by cross-linking molecules of interpenetrating denatured collagen coupled at their lysine epsilon amino groups with a coupler through carbonyl groups, sulfonyl groups, or combination thereof on the coupler wherein non-coupled lysine epsilon amino groups are bonded to a modifier wherein the modifier is a carbonyl, sulfonyl, carbamoyl, or $\beta$-malic acid group. The present invention is also a method for making the membrane and its use in tympanic membrane repair.

The present invention is made by denaturing coupled, and preferably modified, collagen molecules The coupled and modified collagen molecules useful in accordance with the present invention and their method of manufacture are disclosed in U.S. patent application Ser. No. 264,062, filed Oct. 28, 1988 now a U.S. Pat. No. 4,883,864 of Nov. 28, 1989 and Ser. No. 890,847, filed Aug. 6, 1986, now a U.S. Pat. No. 4,713,446 of Dec. 15, 1987 the disclosures of which are incorporated herein by reference. The carbonyl groups, sulfonyl groups, or combination thereof on the coupler are bonded together through an R group wherein R is a $C_{2-20}$ saturated or unsaturated aliphatic, aromatic, or aliphatic-aromatic group that is unsubstituted or substituted with halogen, or $C_{1-4}$ carboxy, alkyl, or alkoxy and having 0-5 heteroatoms wherein the heteroatom is oxygen, sulfur, or nitrogen. Preferably, the coupler has the formula —CO—$CH_2$—$CH_2$— CO— or —CO—$CH_2$—$CH_2$—$CH_2$—$CH_2$—CO—. The modifier has the formula RCO—, RNHCO—, $RSO_2$—, or COOR'CHOHCH(COOR')— wherein R is a $C_{2-20}$ saturated or unsaturated aliphatic or aromatic group that is unsubstituted of substituted with halogen, $C_{1-4}$ alkyl or alkoxy, and having 0-5 heteroatoms wherein the heteroatom is oxygen, sulfur, or nitrogen, and R' is H, Na, K, or Li. Preferably, the modifier has the formula R—NH—CO—, more preferably $CH_3(CH_2)_3$—NH—CO—. Coupling is performed by reacting native collagen with a polyfunctional amine-reactive agent selected from the group consisting of a carboxylic acid halide, sulfonyl halide, anhydride, and reactive active ester in aqueous media at a pH greater than about 8 and at a temperature between 0° and 35° C. Preferably, the poly-functional amine-reactive agent is succinic acid dichloride or glutaric acid dichloride. Preferably, the ratio of poly-functional amine-reactive agent used per weight of native collagen varies between about 1/100 and 6/1, more preferably between about 1/50 and 2/1. Modification involves reacting the native collagen molecules with a mono-functional amine reactive agent selected from the group consisting of an anhydride, acid halide, sulfonyl halide, active ester, isocyanate, and epoxy succinic acid in aqueous media at a pH greater than about 8 and at a temperature between about 0° and 35° C. Preferably, the mono-functional amine-reactive agent is n-butyl isocyanate or epoxy succinic acid. The weight ratio of mono-functional amine-reactive agent used per amount of native collagen is between about 1/100 and 10/1, more preferably between about 1/10 and 1/1. Coupling and modifying are performed in any order, or simultaneously.

Denaturing is preferably performed by heating the coupled and preferably modified collagen molecules in aqueous media or non-aqueous media at a temperature between about 40° and 120° C. Heating causes the normal collagen helix to unwind, producing single stranded collagen molecules coupled at their lysine epsilon amino groups. Upon cooling, the solution forms a gel, which is believed to contain an interpenetrating network of hydrogen bonded $\alpha$-helixes with segments of single stranded collagen exposed.

Accordingly, the heated collagen molecules are cast into a desired shape, such as a film, and then allowed to cool and gel. Preferable thicknesses for the gel are between about 0.127 cm and 1.27 cm, more preferably between about 0.254 cm and 0.613 cm. After cooling, the interpenetrating, denatured collagen molecules are cross-linked to form an artificial membrane useful in tympanic membrane repair. Methods of using the artificial membrane in the surgical repair of tympanic membranes will be apparent to those of ordinary skill in the art.

Preferably, the gel is dehydrated, which is believed to cause some cross-linking of the collagen molecules. After dehydration, the membrane has a preferable thickness between about 0.1 and 0.5 mm, more preferably between about 0.15 and 0.25 mm. Preferably, after dehydration the molecules are further cross-linked to increase the burst strength of the membrane. Further cross-linking is preferably performed by treating the membrane with chemical cross-linking agents or exposing the membrane to sufficient actinic radiation. Useful cross-linking agents include polyfunctional amine reactive agents such as a carboxylic acid halide, sulfonyl halide, anhydride, and reactive ester. Examples of such agents are disclosed in the aforementioned U.S. patent application Ser. No. 890,847. Methods for using chemical cross-linking agents will be apparent to the skilled artisan. Preferably, chemical cross-linking is performed using non-aqueous systems in order to prevent hydrolysis of the cross-linking agent. For example, the membrane is immersed in succinyl chloride, either neat or in pyridine or other suitable organic base that would neutralize HCl evolved during the cross-linking reaction, at an amount of about 0 001–0.1 moles of agent per gram of membrane, preferably about 0.005–0.05 moles/g. Alternatively, chemical cross-linking can be carried out in aqueous media while maintaining a pH of 8–10 and using an amount of cross-linking agent between about 0.05 and 0.5 moles per gram of membrane, depending on the rate of hydrolysis of the particular agent used. Useful forms of actinic radiation include ultraviolet light, gamma radiation, and electron beam radiation Sources and methods of applying radiation to the membrane will be apparent to the skilled artisan. After cross-linking, the membrane is preferably washed to remove unreacted agents, and further sterilized, e.g., by autoclaving or exposure to gamma radiation or ethylene oxide, before use in tympanic membrane repair.

Preferably, the artificial membrane of the present invention is cleaned and purified before use. For example, either before or after heating, but prior to cooling, a solution of the coupled and modified collagen molecules are filtered to remove particles. At any stage in the process after denaturation, extraction purification, e.g., using sterile water for injection, high-purity grade acetone, or other suitable solvent or solvent mixture, can be employed.

Optionally, suture thread or polymerized collagen cut to an appropriate size and shape is embedded into the membrane at a right angle during formation to aid in later placement during surgery. For example, a suture thread can be placed in the freshly cast, heated collagen before cooling so that, when the collagen is cooled and dehydrated, it forms an integral part of the membrane. The suture then provides a useful handle during tympanoplasty. Also, it is advantageous to texturize the membrane using a perforation tool to aid in placement during surgery.

The present invention provides a flexible, yet strong membrane that has low cytotoxicity, good tensile strength, adjustable degradation time, compliance characteristics close to that of a natural tympanic membrane, and a mildly adherent surface that is repositionable on living tissue without excessive sliding.

To more clearly describe the present invention, the following, non-limiting examples are provided. All parts and percentages in the examples are by weight unless indicated otherwise.

EXAMPLE 1

Coupled and modified collagen is prepared by addition of a chemical coupling agent and subsequently an amine modifying agent, using aseptic technique under a laminar flow hood. About 500 ml of chilled (4° C.) Vitrogen TM collagen Type I solution (Collagen Corp., Palo Alto, Calif.) is poured into a glass reactor vessel. The pH of the solution is brought to 9 by the addition of 5N sodium hydroxide. At a temperature between about 4° and 8° C., the solution is vigorously agitated and 0.28 g of succinyl chloride is added all at once to the solution. The reaction is allowed to proceed for 20 minutes, and during this time the pH is held within the range between 9.0 and 9.35 by the gradual addition of 1N sodium hydroxide solution as needed.

The product obtained above is modified with a reagent that covalently binds to the exposed amine groups on the coupled collagen molecules. The vigorous agitation of the solution is continued while 0.35 g of dry butyl isocyanate is added to the vessel as rapidly as possible. The reaction is allowed to proceed for 1 hour, and during this time the pH is held within the range between 9.0 and 9.25 by the addition of 1N sodium hydroxide solution as needed. As the reaction proceeds, the solution is gradually allowed to warm to room temperature. The pH of the solution is then decreased slowly by the addition of 6N hydrochloric acid to precipitate out the modified collagen. The acid is added until the cloudiness of the solution stops increasing (generally at a pH of about 4.0–4.7). The solution is allowed to continue mixing for 5 minutes. The resulting collagen slurry is centrifuged at a temperature of about 4° C., at a speed sufficient to create a force of about 10,000 G (as measured at the bottom of the centrifuge tube), and the supernatant removed.

The resulting collagen precipitate is washed by adding pyrogen free water to a total volume of about 240 ml of collagen suspension, and the pH is adjusted to within the range of 4.5 and 4.7 by the addition of 1N hydrochloric acid or 1N sodium hydroxide as needed. The neutralized collagen suspension is centrifuged at 4° C., at a speed of about 10,000 rpm (16,000 G at the bottom of the centrifuge tube), for 10 minutes. After removing the supernatant, this procedure is repeated three times for a total of four washings. The final collagen concentration is adjusted to approximately 2% by weight.

The washed and modified collagen product is then denatured by heating at 60°–80° C. for one hour in a water bath. The material is then neutralized with 1N sodium hydroxide as needed to bring the pH to within the range of 7.0 to 7.2.

About 6.0 ml of the warm denatured collagen solution is transferred into a sterile flat-bottom polytetrafluoroethylene dish 6 cm in diameter. The side of which has been machined to about a 5°–15° angle outward from the bottom to facilitate subsequent membrane removal, and the bottom of the dish has been machined roughly to create a relief of about a 1.27 $\mu$m in the surface of the membrane. The dish is then covered with a sterile petri dish and allowed to sit at ambient conditions (approximately 23° C.) for 25 minutes to allow the denatured collagen to slowly cool and gel.

The covered dish is then transferred to a pre-purged, nitrogen box having about 70 l total volume. At a nitrogen flow rate of about 12–15 l/minute, the material is dried for about 24–36 hours to form a membrane.

The membrane is laid on an aluminum foil at a distance of 15–16 cm from a 15 Watt, 254 nm, ultraviolet light source for a period of about 4 hours.

The membrane is then purified by immersion in 150 ml of high-purity grade acetone and allowed to sit for a minimum of 2 hours under gentle agitation. The charge of acetone is then decanted and the purification/extraction step repeated twice.

EXAMPLES 2, 3, 4 and 5

Comparison of membranes with various degrees of coupling is made. Membranes are prepared as in EXAMPLE 1 except that the quantity of succinyl chloride employed in the initial coupling reaction is varied from a control using no succinyl chloride, i.e., a non-coupled control, 0.02 ml succinyl chloride per gram of collagen (EXAMPLE 2), 0.04 ml succinyl chloride per gram of collagen (EXAMPLE 3), 0.06 ml succinyl chloride per gram of collagen (EXAMPLE 4), and 0.20 ml succinyl chloride per gram of collagen (EXAMPLE 5), and a hand prepared ultra-pure collagen material prepared according to EXAMPLE 1 of U.S. Pat. No. 4,713,446, is used as the starting material. The hydraulic burst strength of the various membranes is determined by testing a 1.58 cm disk cut from each membrane as in EXAMPLE 1, which is wetted with pyrogen free water and allowed to hydrate for at least ten minutes. Using two pairs of cooperating O-rings, each having a 0.95 cm internal diameter and about 0.3 cm cross-sectional diameter, and applying the minimum force necessary between the cooperating rings, the disk is held in place over a cylinder connected to a syringe pump and a pressure transducer. Air is removed from inside the cylinder to ensure that only hydraulic force from the syringe pump is applied to the membrane Injection-grade water is steadily introduced into the cylinder at 0.388 ml/minute using the syringe pump. The time elapsed to burst of the membrane yields volume of H₂O pumped into the cylinder and the hydraulic pressure is measured by the transducer, which is read directly on a digital read out. The highest pressure attained is recorded as the burst pressure. The results are recorded in the following table. Underlined values are extrapolations to a thickness of 0.072 mm thickness.

| Membrane thickness (mm) | Control | EX 2 | EX 3 | EX 4 | EX 5 |
|---|---|---|---|---|---|
| | | Burst Pressure (kg/cm²) | | | |
| 0.053 | | 0.487 | | | |
| 0.056 | | | | 0.821 | |
| 0.064 | | 0.562 | | 0.949 | |
| 0.065 | | | 0.932 | | |
| 0.072 | 0.443 | 0.605 | 1.223 | 1.111 | 0.872 |
| 0.077 | | 0.696 | | | |
| 0.082 | 0.485 | | | | |
| 0.058 | | | 1.617 | | |
| 0.108 | | | 2.023 | | |
| 0.116 | | 0.765 | | | |

EXAMPLE 6

A membrane is prepared for repairing a 3 mm perforation in the tympanic membrane of a chinchilla. A membrane made according to EXAMPLE 3 having a thickness of 0.058 mm is wetted with sterile, pyrogen-free water and allowed to hydrate for 5 minutes to facilitate cutting. A 1 cm diameter disk is then cut from the membrane using a stainless steel punch die and a small arbor press cutting against a polytetrafluoroethylene surface. The disk is then texturized to create perforations in the membrane by forcing it over pyramidal titanium spikes fixed 500 μm apart in a square pattern on a plate, each spike being about 150 μm² at its base and about 150 μm high. The disk is then allowed to dry for at least one hour. After drying, the membrane is sealed in appropriate packaging and sterilized by exposure to 0.5-0.6 Mrad gamma radiation.

Surgical repair is commenced by making a posterior approach to the bulla of the anesthetized chinchilla. The margin of the perforation in the tympanic membrane is neatened and a region 1.5 mm wide is denuded of epithelium using a half-Hough tool. The artificial membrane disk is removed from its sterilized packaging and trimmed to an appropriate diameter, i.e., such that at least 3.4 mm of the membrane contacts the intact borders of the ruptured eardrum, or about 1.5 times the diameter of the eardrum perforation. The trimmed membrane is positioned over the perforation so that the side of the disk bearing the raised areas formed during texturizing faces the eardrum tissue. Ten minutes are allowed for fibrin formation to completely proceed within the perforations on the disk. Although no sponge packing of the bulla is used, gross movements of the animal performed between about 10 minutes and one hour after surgery do not displace the disk. Tympanometry is performed after several days using a model 6A typanometer (Maico, Minneapolis, Minn.), which shows near normal tympanic membrane function. A histological evaluation of the implants removed after 30 days shows fibroblast infiltration of the areas, as well as the deposition of new type I collagen within the graft matrix.

EXAMPLE 7

A texturized disk prepared as in EXAMPLE 6 is used to close a 2.5 mm perforation in the tympanic membrane of a monkey. A trans-canal approach is made to the damaged tympanic membrane of the anesthetized monkey, the margin of the perforation is neatened, and the epithelium peeled back around its circumference. The disk is trimmed and positioned over the perforation from the middle ear side as in EXAMPLE 6. The edges of the epithelium are then folded over the top of the disk and ten minutes are allowed for fibrin formation to occur within the perforations. Gross movements of the animal as in the previous example do not dislodge the disk, even in the absence of sponge packing.

EXAMPLE 8

The procedure of EXAMPLE 1 is repeated except that dehydration of the denatured collagen gel is omitted, and the gel is exposed to ultraviolet radiation to form the cohesive membrane. When fully hydrated, the membrane thus formed has a greater water content than the membrane of EXAMPLE 1.

Claimed is:

1. An artificial membrane comprising a product made by cross-linking molecules of interpenetrating denatured collagen coupled at their lysine epsilon amino groups with a coupler through carbonyl groups, sulfonyl groups, or combination thereof on the coupler wherein non-coupled lysine epsilon amino groups are bonded to a modifier wherein the modifier is selective from the group consisting of a carbonyl, sulfonyl, carbamoyl, or β-malic acid group.

2. The membrane of claim 1 wherein cross-linking is effected by reacting the molecules with a polyfunctional amine reactive agent selected from the group consisting of a carboxylic acid halide, sulfonyl halide, anhydride, reactive ester, and aldehyde.

3. The membrane of claim 1 wherein cross-linking is effected by exposing the molecules to actinic radiation.

4. The membrane of claim 1 wherein cross-linking is effected by dehydrating a gel containing the molecules.

5. The membrane of claim 1 wherein cross-linking is effected by dehydrating a gel containing the molecules and exposing the dehydrated molecules to actinic radiation.

6. The membrane of claim 1 wherein the coupler comprises the carbonyl groups, sulfonyl groups, or combination thereof bonded together through an organic radical wherein the organic radical is a $C_{2-20}$ saturated or unsaturated aliphatic, aromatic, or aliphatic-aromatic group that is substituted or unsubstituted with halogen or $C_{1-4}$ alkyl, alkoxy, or carboxy and has 0-5 heteroatoms wherein the heteroatom is oxygen, sulfur, or nitrogen.

7. The membrane of claim i wherein the coupler has the formula —CO—CH₂—CH₂—CO— or —CO—CH₂—CH₂—CH₂—CO—.

8. The membrane of claim 1 wherein the modifier has the formula RCO—, RNHCO—, RSO₂—, or COOR'-CHOHCH(COOR')— wherein R is a $C_{2-20}$ saturated or unsaturated aliphatic, aromatic, or aliphatic-aromatic group that is substituted or unsubstituted with halogen or $C_{1-4}$ alkyl, alkoxy, or carboxy and has 0-5 heteroatoms wherein the heteroatom is oxygen, sulfur, or nitrogen and R' is H, Na, K, or Li.

9. The membrane of claim 8 wherein the modifier has the formula R—NH—CO—.

10. The membrane of claim 1 wherein the modifier has the formula $CH_3(CH_2)_3$—NH—CO—.

11. The membrane of claim 1 wherein the modifier has the formula $CH_3(CH_2)_3$—NH—CO— and the coupler has the formula —CO— $CH_2$—$CH_2$—CO—.

12. The membrane of claim 1 wherein the molecules were denatured by heating in aqueous media to a temperature between about 40° and 120° C. and thereafter cooling.

13. An artificial membrane comprising a product made by cross-linking molecules of interpenetrating denatured collagen coupled at their lysine epsilon amino groups with a coupler through carbonyl groups, sulfonyl groups, or combination thereof on the coupler.

14. The membrane of claim 13 wherein cross-linking is effected by reacting the molecules with a polyfunctional amine reactive agent selected from the group consisting of a carboxylic acid halide, sulfonyl halide, anhydride, aldehyde, and reactive ester.

15. The membrane of claim 13 wherein cross-linking is effected by exposing the molecules to actinic radiation.

16. The membrane of claim 13 wherein cross-linking is effected by dehydrating the molecules.

17. The membrane of claim 13 wherein cross-linking is effected by dehydrating the molecules and exposing the molecules to actinic radiation.

18. The membrane of claim 13 wherein the coupler is —CO—$CH_2$—$CH_2$—CO— or —CO—$CH_2$—$CH_2$—$CH_2$—CO—.

19. The membrane of claim 13 wherein the molecules were denatured by heating in aqueous media to a temperature between about 40° and 120° C. and thereafter cooling.

20. A method for making an artificial membrane comprising the steps of:
a) reacting native collagen molecules with a poly-functional amine-reactive agent selected from the group consisting of a carboxylic acid halide, sulfonyl halide, anhydride, and reactive ester in aqueous media at a pH greater than about 8 and at a temperature between 0° and 35° C. to form coupled collagen molecules;
b) heating the coupled collagen molecules at a temperature between about 40° and 120° C. to denature the collagen;
c) purifying the coupled collagen molecules; and
d) cooling and forming the denatured and coupled collagen molecules into a membranous gel.

21. The method of claim 20 further comprising the step of sufficiently dehydrating the gel to cross-link the collagen molecules.

22. The method of claim 20 further comprising the step of reacting the collagen molecules with a polyfunctional amine-reactive agent selected from the group consisting of a carboxylic acid halide, sulfonyl halide, anhydride, and reactive ester after dehydration and subsequently purifying the product.

23. The method of claim 20 further comprising the step of exposing the gel to sufficient actinic radiation to cross-link the collagen molecules.

24. The method of claim 20 further comprising the steps of dehydrating the gel followed by exposing the collagen molecules to sufficient actinic radiation to further cross-link the collagen molecules.

25. The method of claim 20 wherein the weight ratio of poly-functional amine-reactive agent to native collagen molecules is between about 1:100 and 6:1.

26. The method of claim 20 wherein the poly-functional amine reactive agent is succinic acid dichloride or glutaric acid dichloride.

27. The method of claim 20 further comprising the step of reacting the native collagen molecules with a mono-functional amine reactive agent selected from the group consisting of an anhydride, acid halide, sulfonyl halide, active ester, isocyanate, and epoxy succinic acid in aqueous media at a pH greater than about 8 and at a temperature between about 0° and 35° C.

28. The method of claim 27 further comprising the step of sufficiently dehydrating the gel to cross-link the collagen molecules.

29. The method of claim 28 further comprising the step of reacting the collagen molecules with a polyfunctional amine-reactive agent selected from the group consisting of a carboxylic acid halide, sulfonyl halide, anhydride, and reactive active ester after dehydration and subsequently purifying the product.

30. The method of claim 27 further comprising the step of exposing the gel to sufficient actinic radiation to cross-link the collagen molecules 31. The method of claim 27 further comprising the steps of dehydrating the gel followed by exposing the collagen molecules to sufficient actinic radiation to further cross-link the collagen molecules.

32. The method of claim 27 wherein the mono-functional amine reactive agent is n-butylisocyanate.

33. The method of claim 27 wherein the mono-functional amine reactive agent is epoxysuccinic acid.

34. The method of claim 27 wherein the weight ratio of mono-functional amine-reactive agent to native collagen molecules is between about 1:100 and 10:1.

35. A composition comprising molecules of interpenetrating denatured collagen coupled at their lysine epsilon amino groups with a coupler through carbonyl groups, sulfonyl groups, or combination thereof on the coupler wherein non-cross-linked lysine epsilon amino groups are bonded to a modifier wherein the modifier is selective from the group consisting of a carbonyl, sulfonyl, carbamoyl, or β-malic acid group.

36. A composition comprising molecules of interpenetrating denatured collagen coupled at their lysine epsilon amino groups with a coupler through carbonyl groups, sulfonyl groups, or mixture thereof on the coupler.

37. In a method for repairing the tympanic membrane of a mammal comprising surgically applying an artificial membrane over the tympanic membrane the improvement wherein the artificial membrane comprises the artificial membrane of claim 1.

38. In a method for repairing the tympanic membrane of a mammal comprising surgically applying an artificial membrane over the tympanic membrane the improvement wherein the artificial membrane comprises the artificial membrane of claim 13.

* * * * *

UNITED STATES PATENT AND TRADEMARK OFFICE
CERTIFICATE OF CORRECTION

PATENT NO. : 5,141,747
DATED : August 25, 1992
INVENTOR(S) : Matthew T. Scholz

It is certified that error appears in the above-indentified patent and that said Letters Patent is hereby corrected as shown below:

Col. 2, Line 60, "0 001" should read --0.001--.

Col. 5, TABLE, "0.443, 0.605, 1.223, 1.111" should read --0.443  0.605  1.223  1.111--.

Col. 6, Lines 33-34, delete "selective from the group consisting of".

Col. 6, Line 58, "i" should read --1--.

Col. 8, Line 47, delete "selective from the group consisting of".

Signed and Sealed this

Twenty-fifth Day of October, 1994

Attest:

BRUCE LEHMAN

Attesting Officer

Commissioner of Patents and Trademarks